United States Patent
Lay

(10) Patent No.: US 11,839,756 B2
(45) Date of Patent: Dec. 12, 2023

(54) CONDUCTIVE CIRCUIT

(71) Applicant: Atlantic Therapeutics Group Limited, Galway (IE)

(72) Inventor: Graham Robert Lay, Newmarket (GB)

(73) Assignee: Atlantic Therapeutics Group Limited, Galway (IE)

(*) Notice: Subject to any disclaimer, the term of this patent is extended or adjusted under 35 U.S.C. 154(b) by 0 days.

(21) Appl. No.: 16/766,182

(22) PCT Filed: Dec. 4, 2018

(86) PCT No.: PCT/EP2018/083506
§ 371 (c)(1),
(2) Date: May 21, 2020

(87) PCT Pub. No.: WO2019/110595
PCT Pub. Date: Jun. 13, 2019

(65) Prior Publication Data
US 2020/0360681 A1 Nov. 19, 2020

(30) Foreign Application Priority Data

Dec. 4, 2017 (GB) .................................. 1720164
Sep. 26, 2018 (GB) .................................. 1815690
Nov. 13, 2018 (GB) .................................. 1818461

(51) Int. Cl.
*A61N 1/04* (2006.01)
*A61N 1/36* (2006.01)

(52) U.S. Cl.
CPC ......... *A61N 1/0452* (2013.01); *A61N 1/0484* (2013.01); *A61N 1/36007* (2013.01)

(58) Field of Classification Search
None
See application file for complete search history.

(56) References Cited

U.S. PATENT DOCUMENTS 6,944,503 B2   9/2005  Crowe
7,504,550 B2   3/2009  Tippey
(Continued)

FOREIGN PATENT DOCUMENTS

GB        2555592        5/2018
JP        2001057967     3/2001
(Continued)

OTHER PUBLICATIONS

International Patent Application No. PCT/EP2018/083506, International Preliminary Report on Patentability, dated Jun. 9, 2020, 10 pages.
(Continued)

*Primary Examiner* — Catherine M Voorhees
*Assistant Examiner* — Elizabeth K So
(74) *Attorney, Agent, or Firm* — Fitch Even Tabin & Flannery LLP

(57) ABSTRACT

The invention provides a conductive circuit which may be applied to a garment, for example a garment for the stimulation of pelvic floor muscles. In the illustrated embodiments in the garment comprises a pair of shorts. The shorts are made from stretch fabric comprising a polyamide and are designed to fit closely to the body. The shorts are provided with two legs and a waistband area. The shorts comprise left and right conductive circuits, each of which comprises one or more electrodes formed from a printed conductive layer.

13 Claims, 7 Drawing Sheets

(56) References Cited

U.S. PATENT DOCUMENTS

| | | | |
|---|---|---|---|
| 8,494,658 | B2 | 7/2013 | Crowe |
| 8,739,397 | B2 | 6/2014 | Nagata |
| 9,386,684 | B2 * | 7/2016 | Sime .............. A61B 5/282 |
| 9,545,514 | B2 | 1/2017 | Minogue |
| 9,675,802 | B2 | 6/2017 | Crowe |
| D847,457 | S | 5/2019 | Piombino |
| 10,315,402 | B2 | 6/2019 | Brook |
| D864,523 | S | 10/2019 | Diamond |
| D917,127 | S | 4/2021 | Chisholm |
| D922,730 | S | 6/2021 | Bae |
| D939,189 | S | 12/2021 | De Mulder |
| D953,694 | S | 6/2022 | Zhang |
| 2002/0077688 | A1 | 6/2002 | Kirkland |
| 2013/0060115 | A1 | 3/2013 | Gehman |
| 2013/0248226 | A1 | 9/2013 | Sime |
| 2015/0040282 | A1 | 2/2015 | Longinotti-Buitoni |
| 2015/0366504 | A1 * | 12/2015 | Connor .............. A61B 5/6804 600/301 |
| 2016/0374615 | A1 | 12/2016 | Tsukada |
| 2017/0182320 | A1 | 6/2017 | Kolb |
| 2019/0132948 | A1 | 5/2019 | Longinotti-Buitoni |
| 2020/0353239 | A1 * | 11/2020 | Daniels .............. A61N 1/02 |
| 2021/0100681 | A1 | 4/2021 | Miles |
| 2021/0298369 | A1 | 9/2021 | Polstein |
| 2022/0152380 | A1 | 5/2022 | Lay |

FOREIGN PATENT DOCUMENTS

| | | |
|---|---|---|
| JP | 2003250914 | 9/2003 |
| JP | 2010502251 | 1/2010 |
| JP | 2010220754 | 10/2010 |
| WO | 2003006106 | 1/2003 |
| WO | 2007138071 | 12/2007 |
| WO | 2008088985 | 7/2008 |
| WO | 2012116407 | 9/2012 |
| WO | 2017075703 | 5/2017 |
| WO | 2018055207 | 3/2018 |
| WO | 2018098046 | 5/2018 |
| WO | 2020239950 | 12/2020 |

OTHER PUBLICATIONS

International Patent Application No. PCT/EP2018/083506, International Search Report, dated Mar. 7, 2019, 5 pages.

Description of INNOVO® shorts, <https://www.myinnovo.com/uk/healthcare-professionals/clinical-studies/innovo-strengthens-the-entire-pelvic-floor-musculature>, dated Jan. 21, accessed Nov. 25, 2019, 4 pages.

Screenshot—The INNOVO Story with Dr. Ruth Maher & Dr. Sherry Ross, INNOVO, <https://www.youtube.com/watch?v=Pm6rAOwnPBo>, uploaded May 30, 2019; see especially 2:09, 1 page.

Notification of Reasons for Refusal, Japanese Patent Application No. 2020-547314, dated Nov. 22, 2022, (with English translation), 18 pages.

Choosing the Best Prolapse Support Garment, posted Jan. 7, 2019 [online], (retrieved Jun. 21, 2022). Retrieved from the internet, https://www.femicushion.com/blogs/femicushion/how-to-choose-the-right-prolapse-support-garment (Year: 2019).

In NOVO Kegel Exerciser, posted NA [online], (retrieved Jun. 21, 2022). Retrieved from the internet, https://www.myinnovo.com/products/innovo-starter-kit (Year: NA).

Vulvar Varicosity and Prolapse , reviewed Jun. 21, 2021 posted NA [online], (retrieved Jun. 21, 2022). Retrieved from the internet,https://www.underworks.com/vulvar-varicosity-and-prolapse-support-brief-with-g roi n-compression-bands-with-hot-cold-therapy-gel-pad?gclid=EAlalQobChMI_M-cuPO-AIVhfLjBx3EzwHSEAkY (Year: 2021).

* cited by examiner

CONDUCTIVE CIRCUIT

TECHNICAL FIELD

This invention relates to a conductive circuit, particularly for use on or in garments.

BACKGROUND

It is known in the prior art to use external electric stimulation to improve muscle condition. Such devices are described in, for example WO03006106. The use of such devices may to develop muscle tone, either for cosmetic purposes or for the treatment of medical conditions. One condition for which treatment of this nature may be effective is incontinence, as described in WO2007138071. In such devices, targeted impulses are sent via conductive pads producing over 180 contractions per session. The pelvic floor muscles are contracted, improving muscle strength and control, directly targeting a primary cause of stress urinary incontinence. It is currently estimated that over 5 million women in the UK experience the symptoms of urinary incontinence and of these, half of all sufferers aged between 18 and 65 years of age are moderately or greatly bothered by it. About one third of women experience urinary incontinence after giving birth, and over 65% of these women are still affected by it 12 years later. 23% of women with urinary incontinence say that it reduces their activity level; 23% state that it adversely affects their sex life; and 31% dress differently because of their symptoms. Whilst pelvic floor disorders mainly affect women, they can also affect men.

It is important that the impulses are correctly delivered, to target the correct muscles. Whilst currently offered devices are effective when used correctly, they are generally quite hard to position properly. The current devices comprise two neoprene wraps, each having four sticky conductive pads that must be strapped around the upper thighs and buttocks. Some patients find them difficult to position accurately.

It would be advantageous to provide alternative devices that are easy to use and that effectively deliver current to the correct muscles.

SUMMARY OF THE INVENTION

A first aspect of the invention provides a conductive circuit comprising one or more electrodes for transferring an electromagnetic signal to a human or animal body, the one or more electrodes each comprising a base and at least one printed conductive layer. In use, a printed conductive layer is configured to contact the skin of a human or animal body.

Similarly, a first aspect of the invention provides an electrode for transferring an electromagnetic signal to a human or animal body, the electrode comprising a base and at least one printed conductive layer.

The conductive circuit is primarily intended for use in garments for humans, though other uses are possible.

In an embodiment, the base is a support for the conductive layer. The base may be any appropriate structure, for example it may also be a layer. In one embodiment, the base is a fabric, particularly a stretch fabric. A stretch fabric is any fabric that may be reversibly stretched in at least one direction. Stretch fabrics include, for example, fabrics comprising elastane. The fabric may, for example, be a fabric comprising a polyamide or a polyurethane.

The conductive layer is a printed conductive layer. It may comprise a conductive ink. The conductive ink may be any appropriate conductive ink, such as an ink comprising silver, silver chloride or copper.

The conductive layer may be applied directly to the base, or further layers may be applied between the conductive layer and the base. In one embodiment, the electrode further comprises an adhesive layer. The adhesive layer may be applied between the base and the conductive layer. It may be applied by any appropriate means, including printing.

The conductive layer may take any desired shape or configuration. For example, it may be a solid layer. Alternatively, it may be in the shape of a mesh or grid. For example, the layer may be in the form of a grid made up of connected triangles, squares, hexagons or other shape. That is, the conductive layer may comprise a plurality of links interconnected at nodes to define an array of regions in which the conductive layer is not present. Such regions may have any shape, but preferably have a uniform shape or shapes arranged in a uniform repeating pattern. For example, the regions may be triangular, square, hexagonal or any other shape. The links may have a width of between 0.1 and 1 mm and a length of between 2 and 8 mm, for example.

In an embodiment, the electrode may comprise more than one conductive layer, particularly more than one printed conductive layer. Where the electrode comprises more than one conductive layer, the layers may be made of the same conductive material or may comprise different conductive materials. The layers may have the same conductivity or different conductivities.

In an embodiment, the electrode comprises a first conductive layer and a second conductive layer. Preferably, the first and second conductive layers are directly adjacent one another. The first conductive layer may be in the form of a grid or a mesh as defined above. The first conductive layer may comprise or consist of a first conductive material. The second conductive layer may be a solid layer. The second conductive layer may comprise or consist of a second conductive material. The two conductive materials may have the same level of conductivity or different conductivities. For example, the second conductive layer may have a lower conductivity (i.e. higher resistivity) than the first conductive layer. In preferred embodiments the first and second conductive layers each have a higher conductivity than other layers of the electrode.

Accordingly, one embodiment of the invention provides a conductive circuit comprising one or more electrodes for transferring an electromagnetic signal to a human or animal body, the one or more electrodes each comprising a base, a first printed conductive layer and a second printed conductive layer, wherein the two printed conductive layers comprise or consist of materials having different conductivities. In that embodiment, the first conductive layer is arranged between the base layer and the second conductive layer. The second conductive layer is arranged to contact the skin of the user, in use. Other layers may be arranged between the base layer and the first conductive layer.

The first conductive layer is arranged in a mesh or grid pattern, preferably a mesh or grid pattern as defined above. The first conductive layer comprises or consists of a material that is more conductive (i.e. has a higher conductivity and lower resistivity) than the material forming the second conductive layer. For example, the first layer may comprise silver or consist of an ink comprising silver.

The second conductive layer is a solid or substantially solid layer. That is, the second conductive layer is preferably unbroken and continuous in regions in which it overlaps with the first conductive layer. Similarly, the second conductive layer preferably has a uniform cross-section, i.e. a through-thickness that is substantially uniform. The second conductive layer may comprise or consist of carbon.

In some embodiments the second conductive layer may overlap with a portion of the first conductive layer, whereas in other embodiments the second conductive layer may overlap with substantially all of the first conductive layer. For example, the second conductive layer may comprise a continuous band extending around a periphery of the first conductive layer, with a central portion of the first conductive layer exposed. In such arrangements both the second conductive layer and first conductive layer may contact the skin of the user, in use. That is, in regions in which the second conductive layer is present the second conductive layer contacts the skin of the user in use, whereas in regions in which the second conductive layer is not present the first conductive layer contacts the skin of the user in use.

An advantage of providing two such layers is that a more expensive, highly conductive material used to form the first conductive layer may be used more sparingly, forming a grid or mesh, rather than a solid layer. However, the present inventors have identified that such a mesh arrangement used on its own may in some configurations pose the problem of transferring current directly from the layer to a point of low resistance on the skin of a user (for example, from an intersection on the mesh (i.e. a node at which two or more links of the mesh join) to a sweat gland on the skin), resulting in the delivery of more current than is desirable to a small area. By applying a solid or substantially solid layer of more resistive material over all or a portion of the first conductive layer, the current is spread out, and is less likely to be transferred to a specific point.

The one or more electrodes may each further comprise one or more non-conductive layers. The one or more non-conductive layers comprise one or more layers of non-conductive material, such as a printed non-conductive layer. The one or more non-conductive layers may be provided between the conductive layer and the base. In embodiments comprising an adhesive layer the one or more non-conductive layers may be provided between the adhesive layer and the conductive layer. Preferably, the one or more non-conductive layers have a higher resistivity (i.e. lower conductivity) than both the first and second conductive layers.

The conductive circuit may further comprise one or more connection tracks, each connection track providing an electrically conductive path between a respective one of the one or more electrodes and an electrical contact for connection to a controller arranged to supply an electrical signal to the one or more electrodes. Each of the one or more connection tracks may comprise a printed conductive layer on the base, the printed conductive layer being electrically connected to the printed conductive layer of a respective one of the one or more electrodes. For example, the printed conductive layer of the or each connection track may be contiguous with the printed conductive layer of the respective one of the one of more electrodes.

The one or more connection tracks may comprise more than one conductive layer, especially more than one printed conductive layer. The connection tracks may comprise 2, 3, 4, 5 or more conductive layers.

In some embodiments a further non-conductive layer may be provided over a part of the conductive layer of the or each of the one or more electrodes to encapsulate that part of the conductive layer and leave one or more portions of the conductive layer exposed. The one or more exposed portions may be provided in a pattern or arrangement that provides the desired shape and position of regions in which electrical connection to the user's skin is desired.

Each of the one or more connection tracks may comprise one or more non-conductive layer. The one or more non-conductive layers comprise one or more layers of non-conductive material, such as a printed non-conductive layer. The one or more non-conductive layers may be provided between the conductive layer and the base. In embodiments comprising an adhesive layer the one or more non-conductive layers may be provided between the adhesive layer and the conductive layer. The one or more non-conductive layers may be also, or alternatively, provided over the conductive layer to encapsulate the conductive layer. The conductive layer thus may be sandwiched between non-conductive layers.

One or more non-conductive layers provided over the conductive layer of the one or more connection tracks may be provided over all of the conductive layer or over part the conductive layer to leave one or more portions of the conductive layer exposed. For example, an exposed portion may provide an electrical contact for providing an electrical connection between a controller arranged to supply an electrical signal to the one or more electrodes via the one or more connection tracks.

The one or more non-conductive layers may be applied to provide conductive areas and insulated areas. For example, the one or more non-conductive layers may be applied between the base and the conductive layer. The one or more non-conductive layers may be applied between the adhesive layer and the conductive layer. The one or more non-conductive layers may also be applied over parts of the conductive layer, such that at least parts of the conductive layer are between a non-conductive layer and the base, so as to define particular conductive regions.

In an embodiment, the conductive circuit may comprise at least one, at least two, at least three, at least four or at least five conductive regions and/or electrodes. The term conductive region or electrode (these terms being used interchangeably herein) means an area in which the conductive layer is exposed, allowing an electromagnetic signal to be passed to any part of the user's body that is in contact with it, when the conductive circuit is in use. In one embodiment, the conductive circuit has one, two, three, four, five, six, seven, eight, nine, ten or more conductive regions or electrodes.

In an embodiment, the application of the conductive and/or other layers to the fabric alters the modulus of the fabric. In particular, it increases the modulus, such that the fabric is harder to stretch in the areas on which the conductive and/or other layers are applied. For example, the conductive and/or non-conductive layers comprised in the one or more electrodes may increase the modulus in the region of the one or more electrodes.

In an embodiment, the conductive circuit is provided with a means to connect the one or more electrodes to a power supply, controller, or control unit, to control the delivery of power to the one or more electrodes. The means may include one or more contact regions of the conductive circuit in which the conductive layer is exposed to permit an electrical connection thereto. The means may further include a connector configured to provide an electrical connection between the one or more contact regions and the power supply, controller, or control unit. The connector may comprise a first rigid portion durably connected to the conductive circuit, and a second portion having a connected configuration in which an electrical connection between the one or more contact regions and the power supply, controller, or control unit is provided, and an unconnected configuration in which such an electrical connection is prevented. The connector may further include a sheet of deformable material, such as an elastomeric material (e.g. rubber), sandwiched between the first rigid portion and the fabric. The connector may further include one or more magnets configured to facilitate connection between the first and second rigid portions.

A second aspect of the invention provides a garment, comprising at least one conductive circuit according to the first aspect. The garment may comprise more than one electrode, for example, it may comprise two, three, four, five, six, seven, eight or more electrodes. The garment may comprise one or more electrodes with one or more conductive regions. For example, the garment may comprise at least two, three, four, five, six, seven, eight, nine, ten or more conductive regions. In use, the electromagnetic signal may pass from one electrode to another, and/or from one or more electrodes of one conductive circuit to one or more electrodes of another conductive circuit.

The electrode may be applied to the garment, or fabric of the garment may form the base of the electrode.

In an embodiment, the garment is for the lower body. For example, the garment may be trousers or shorts. When the garment is for the lower body, the conductive regions may be provided, for example, on the calves, thighs and/or buttocks. In one embodiment, the conductive regions are provided on the thighs, particularly the back and sides of the thighs and buttocks. The garment may comprise two conductive circuits, a first conductive circuit having one or more electrodes or conductive regions for the left side of the body, and a second conductive circuit having a corresponding one or more electrodes or conductive regions for the right side of the body. There are preferably no seams that dissect either the left or right conductive circuit. The garment may further comprise a left panel carrying the first conductive circuit and a right panels carrying the second conductive circuit. The left and right panels preferably encircle the left and right thighs, respectively, in use. The left and right panels are preferably joined to one another by one or more seams in the crotch and/or inner thigh region. There are preferably no further panels or seams in the outer thigh or buttocks region.

In other embodiments, the garment is for the upper body or for the limbs.

In an embodiment, the conductive regions are provided on both sides of the garment, so that the regions are positioned on both the left and right sides of the body when in use. The conductive regions may arranged so as to be substantially symmetrical about the mid-sagittal plane of the human body when in use.

In preferred arrangements the garment includes one or more visual indicators configured to be aligned with a known body feature in use to thereby ensure correct positioning of the one or more electrodes.

The garment may further comprise a power supply for delivering power to the one or more electrodes.

The garment may further comprise a control unit, or controller, for controlling the delivery of power to the electrode. The power supply and control unit may be provided as one unit.

The garment may further comprise one or more sensors, for example to provide information about the user of the garment. Examples of sensors include an accelerometer, to provide information about the position of the user when using the garment; a thermometer; a sensor to detect muscle contraction; a sensor to detect heart rate or provide other cardiac data; a sensor to detect glucose; or any sensor to detect any other desired physiological characteristic.

A third aspect of the invention provides a kit comprising a conductive circuit according to the first aspect and a power supply and/or control unit or controller.

Similarly, a related aspect of the invention provides a kit comprising a conductive circuit according to the first aspect and a base to which the conductive circuit is to be applied. The conductive circuit may be provided on a substrate and be transferrable to the base by a transfer process, such as by the application of heat and/or pressure. The base may comprise a fabric as disclosed above. Similarly, the base may comprise a garment or a component of a garment such as a panel for use in manufacture of a garment.

A fourth aspect of the invention provides an electrode, garment, or kit according to the earlier aspects of the invention for the use in stimulating muscle activity; detecting muscle stimulation, contraction or relaxation; or treating incontinence, particularly stress incontinence. Also provided is a method of stimulating muscle activity; detecting muscle stimulation, contraction or relaxation; or treating incontinence, particularly stress incontinence, comprising delivering electric current to a patient using an electrode, garment or kit of the invention.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which.

DETAILED DESCRIPTION

Figure 1:
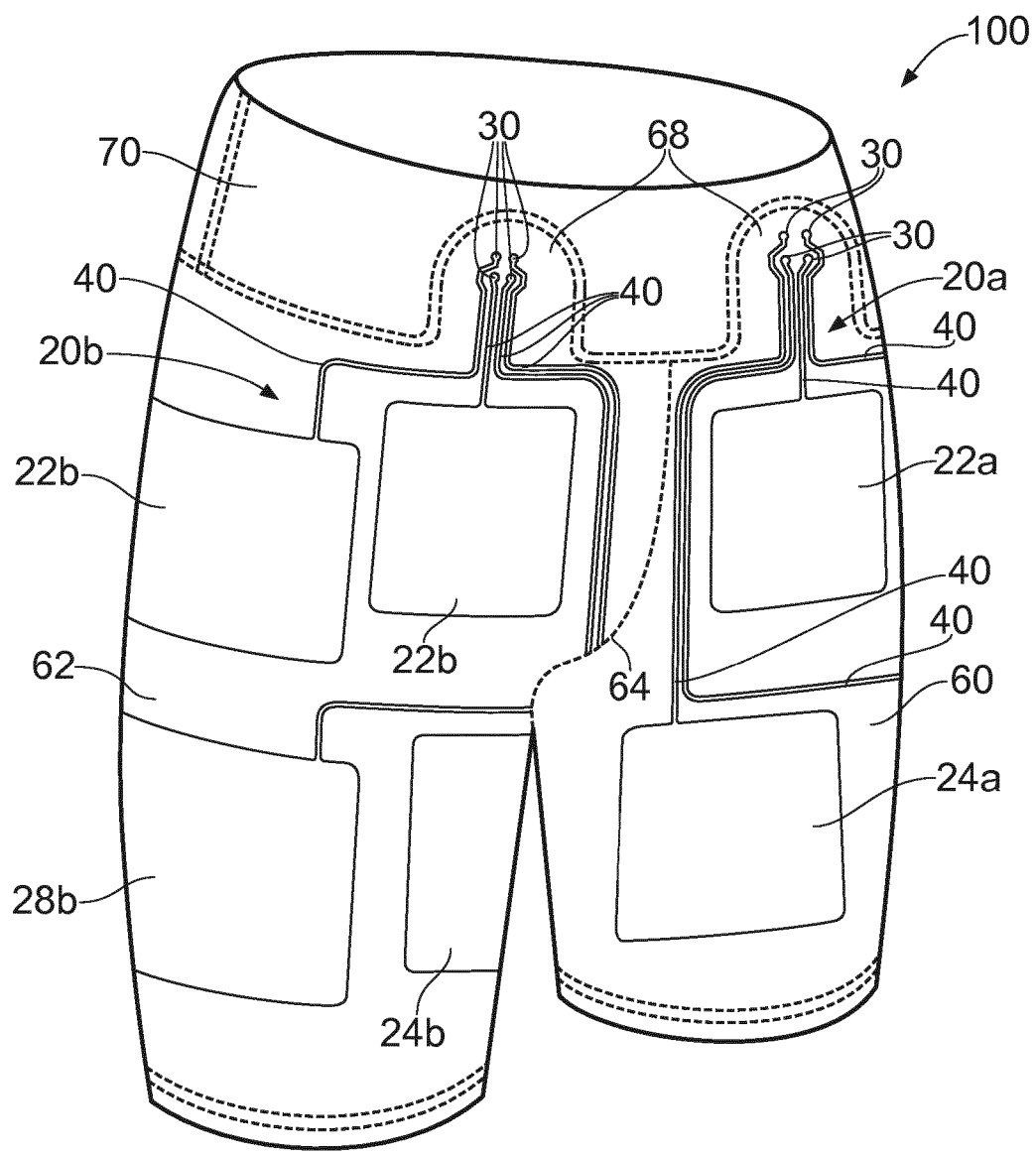
FIG. 1 is a perspective view of a garment according to an embodiment of the invention, showing a conductive circuit printed on an inside surface thereof.
Figure 2:
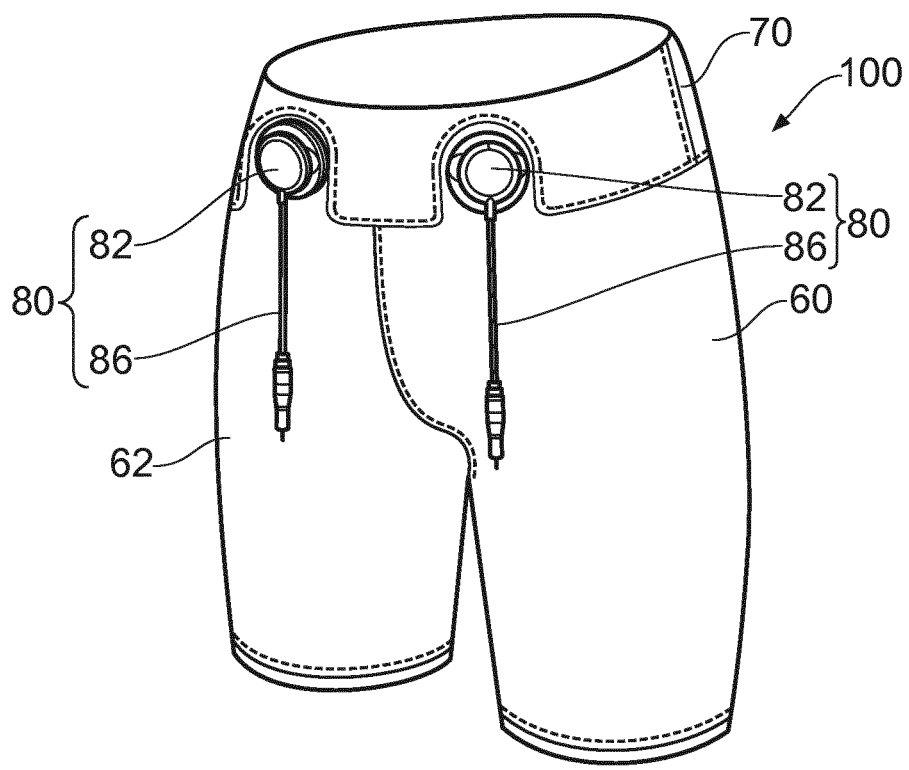
FIG. 2 is a perspective view of a garment according to an embodiment of the invention, with electrical connectors and cables attached thereto.
Figure 3:
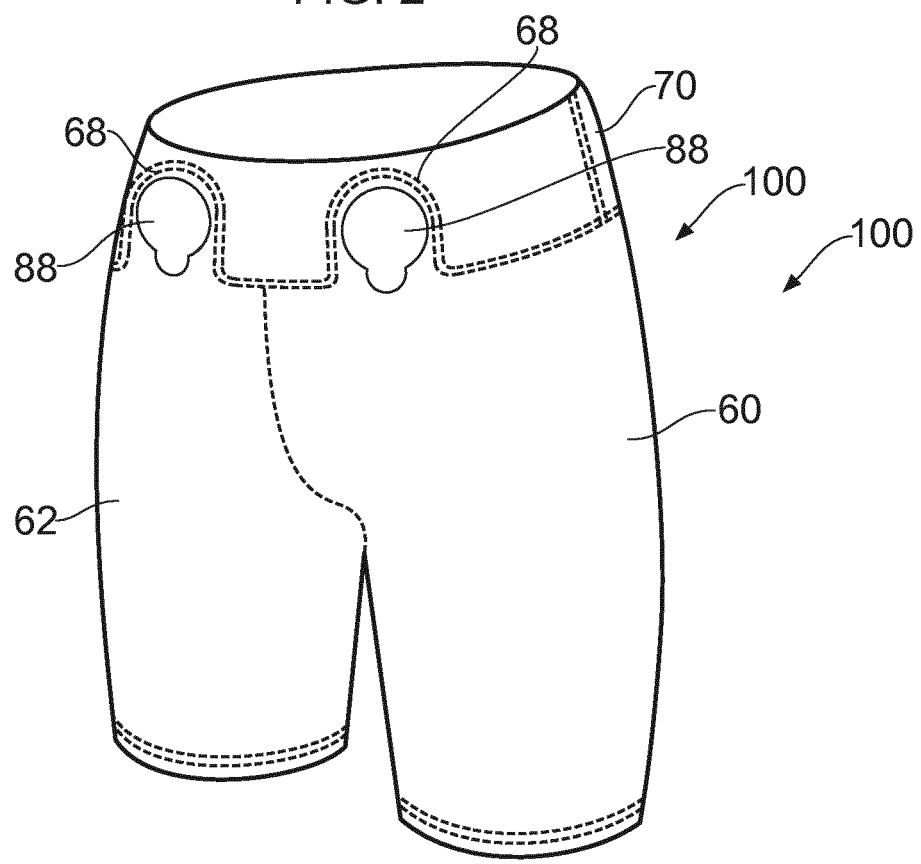
FIG. 3 is a perspective view of the garment of FIG. 2 with electrical connectors and cables omitted.
Figure 4:
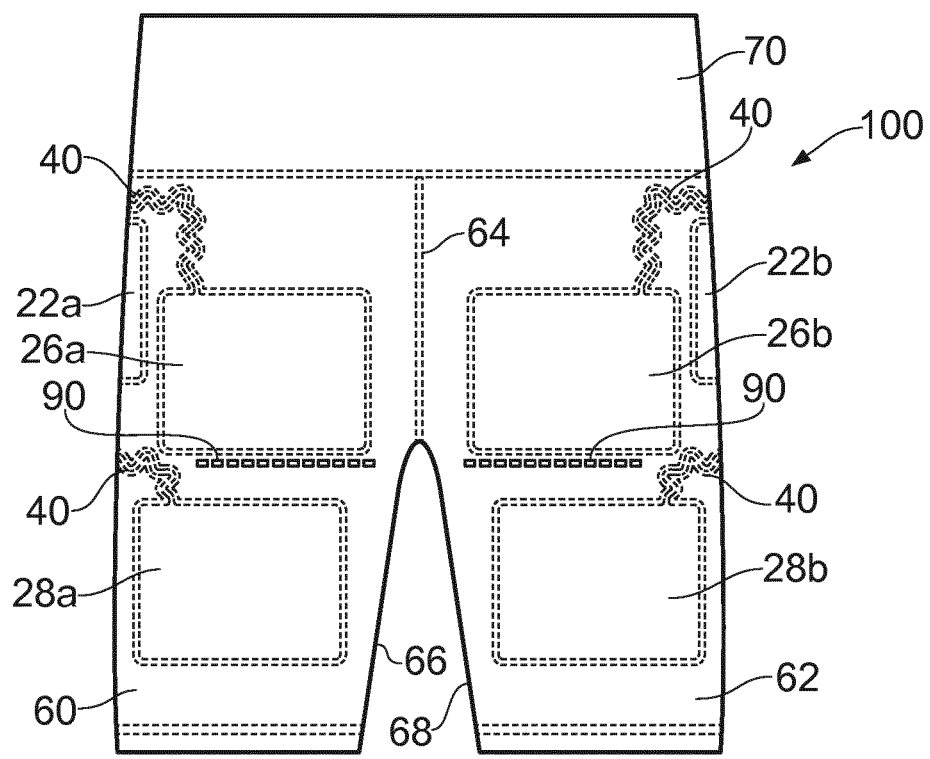
FIG. 4 is a rear view of the garment of FIG. 2, showing a conductive circuit printed on an inside surface thereof.
Figure 5:
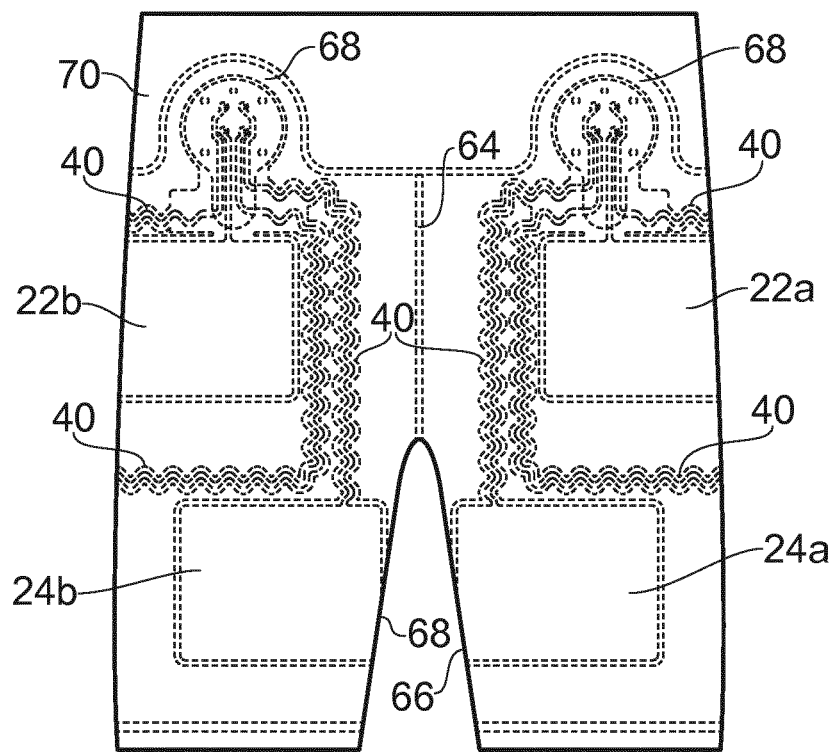
FIG. 5 is a front view of the garment of FIG. 2, showing a conductive circuit printed on an inside surface thereof.
Figure 6:
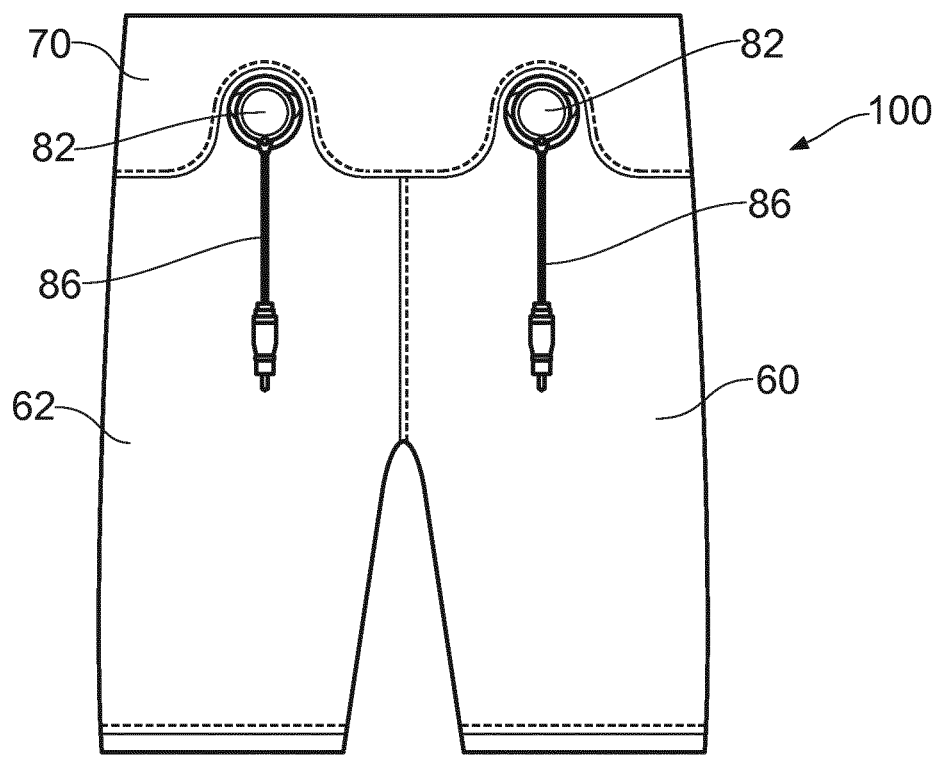
FIG. 6 is a front view of the garment of FIG. 2.
Figure 7:
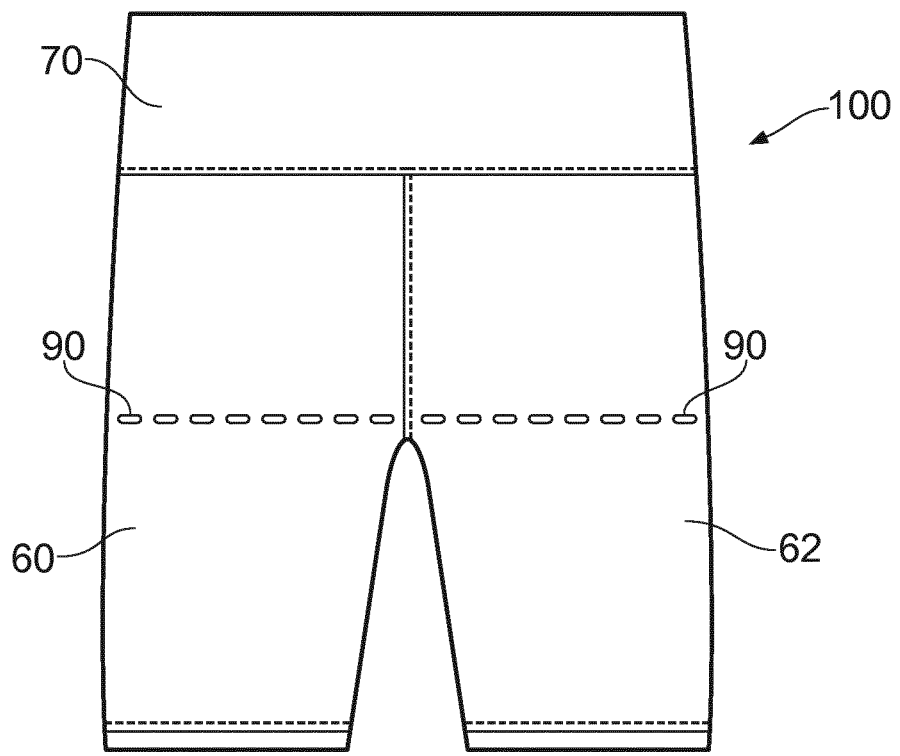
FIG. 7 is a rear view of the garment of FIG. 2.
Figure 8:
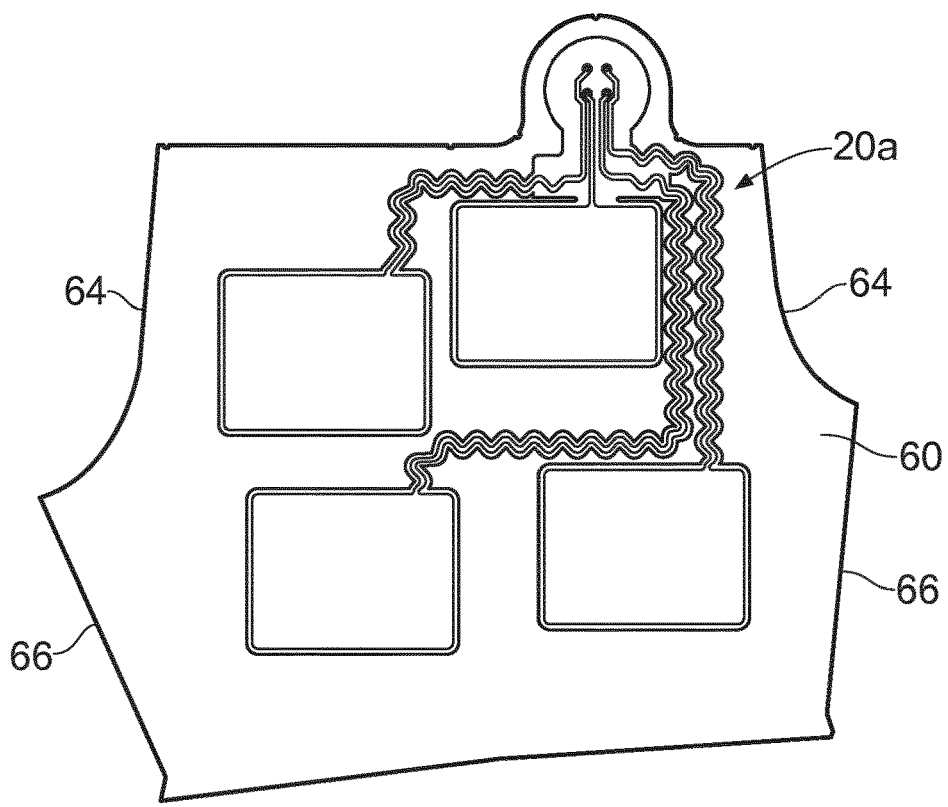
FIG. 8 is a view of an inside surface of a panel for making up a left portion of the garment of FIG. 2.
Figure 9:
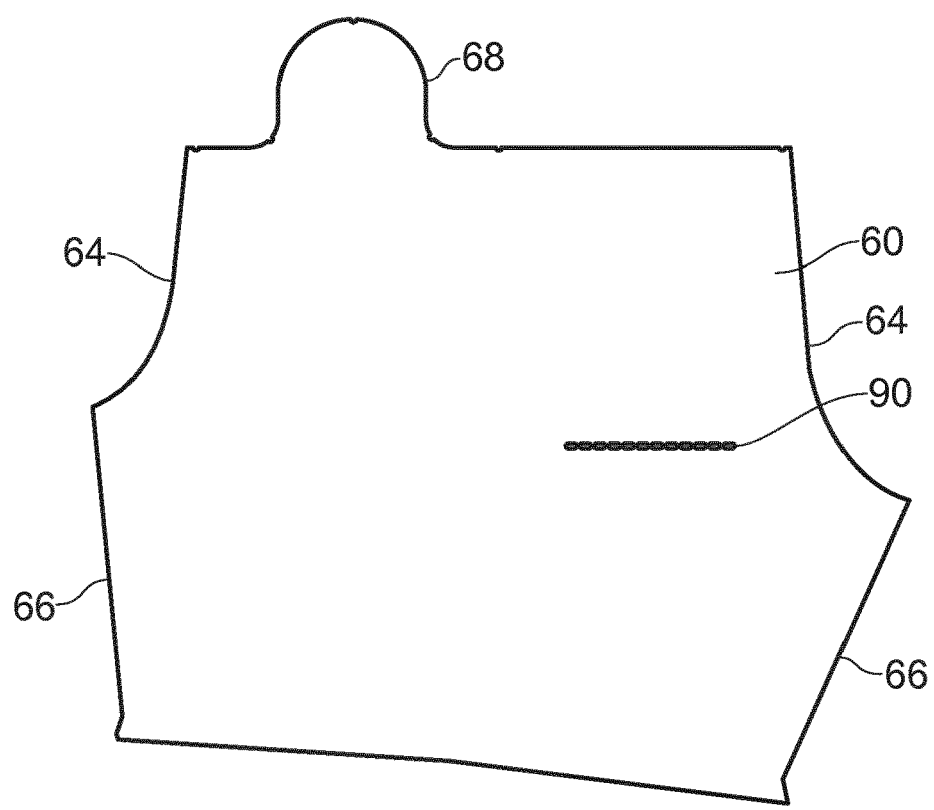
FIG. 9 is a view of an outside surface of the panel of FIG. 8.

The invention provides a conductive circuit which may be applied to a garment, for example a garment for the stimulation of pelvic floor muscles. In the embodiments illustrated in FIGS. 1 to 11 the garment comprises a pair of shorts 100. The shorts 100 are made from stretch fabric comprising a polyamide and are designed to fit closely to the body. The shorts are provided with two legs and a waistband area.

The shorts 100 comprise left and right conductive circuits 20a, 20b. The left conductive circuit 20a is provided in a left leg panel 60 of the shorts 100 and the right conductive circuit 20b is provided in a right leg panel 62 of the shorts 100. The left leg and right leg panels 60, 62 are joined together by a crotch seam 64 that extends from a rear portion of the waistband 70 to a front portion of the waistband 70, and left and right inner leg seams, 66, 68. There are no further seams joining the left leg and right leg panels 60, 62 that extend generally or substantially vertically. In this way, each conductive circuit 20a, 20b is contained within a single panel of fabric, and neither conductive circuit 20a, 20b crosses a seam of the shorts 100.

Each conductive circuit 20a, 20b comprises four electrodes 22, 24, 26, 28 comprising areas of the circuit in which a conductive area of the circuit is arranged to contact the skin of a wearer. The electrodes 22, 24, 26, 28 are each electrically connected to a respective one of eight electrical contact points 30 by a respective conductive track 40. Thus, four of the electrical contact points 30 comprise part of the left conductive circuit 20a, and the remaining four electrical contact points 30 comprise part of the right conductive circuit 20b.

The four electrical contact points 30 for each conductive circuit 20a, 20b are each clustered together towards the top of the respective leg panel 60, 62 in the region of the waistband 70. In the illustrated embodiments each leg panel 60, 62 comprises a tab portion 68 that, when assembled into the shorts 100, extends into the waistband area. Each tab portion 68 carries the respective cluster of electrical contact points 30 for a respective one of the conductive circuits 20a, 20b. In this way, connection to the controller (not shown) via the connecting apparatus (described below) can be achieved in the waistband area, which has been found to be particularly comfortable for users. Moreover, the tab portions 68 comprise a unitary part of each leg panel 60, 62, thereby avoiding the need for any seams crossing the conductive circuits 20a, 20b; seams have been found to adversely affect the electrical resistance of the circuit.

Each electrode is positioned relative to the shorts 100, and in particular relative to its respective leg panel 60, 62, so that it is in contact with a specific region of a user's body when worn. The electrodes 22, 24, 26, 28 are generally located so that they are in contact with the user's skin in the region of the pelvis, to thereby apply a muscular stimulation current which flows laterally across the midline of the user through the user's pelvic floor. That is, current is passed across the pelvis from one leg/hip region to the other via the pelvic floor. Thus, each leg of the shorts is provided with four conductive areas, arranged to contact the skin on the thighs and buttocks of a user when the shorts are worn. The eight conductive areas thus together provide four electrodes for each leg of the shorts.

In alternative embodiments a plurality of the electrodes 22, 24, 26, 28 may be provided as discrete conductive areas exposed within a single region of encapsulating non-conductive material. For example, in such alternative embodiments one electrode may be provided with three conductive areas for providing electrical connections to three discrete areas of a user's skin, and a separate electrode may comprise one such conductive area.

In the illustrated embodiments the first pair of electrodes 22a, 22b are located in the region of a user's hip, the second pair of electrodes 24a, 24b are located generally in the region of a user's upper anterior (front) thigh, the third pair of electrodes 26a, 26b are located generally in the region of the user's buttock, and the fourth pair of electrodes 28a, 28b are located generally in the region of the user's upper posterior (rear) thigh. A visual line 90 is provided on each of the left and right leg panels 60, 62 to provide the user with a visual guide to help ensure correct location of the electrodes 22, 24, 26, 28. The visual line 90 should be aligned with the gluteal crease (also referred to as the gluteal sulcus or gluteal fold) that divides the buttocks from the posterior upper thigh.

In the illustrated embodiments the conductive circuits 20a, 20b are each a mirror image of the other, but in other embodiments the layout of the conductive circuits 20a, 20b could be varied so that they differ from one another. In particular, the route and shape of the tracks 40 may be different on each leg panel 60, 62. In most embodiments it is expected that the position and shape of the left and right electrodes 22, 24, 26, 28 will be mirror images of one another.

In the arrangements illustrated in FIGS. 2-9 the tracks 40 have a generally wavy, or waveform, shape such that the path of each track generally zig-zags between the respective electrode 22, 24, 26, 28 and electrical contact 30. This arrangement has been found to be particularly beneficial because the waveform shape of the tracks 40 allows for the fabric of the leg panel 60, 62 to be stretched during use of the shorts 100 without unduly affecting the electrical resistance provided by the tracks 40. That is, the wavelength and/or amplitude of the waveform can vary to thereby minimise stretching of the one or more conductive layers of the track.

Figure 10:
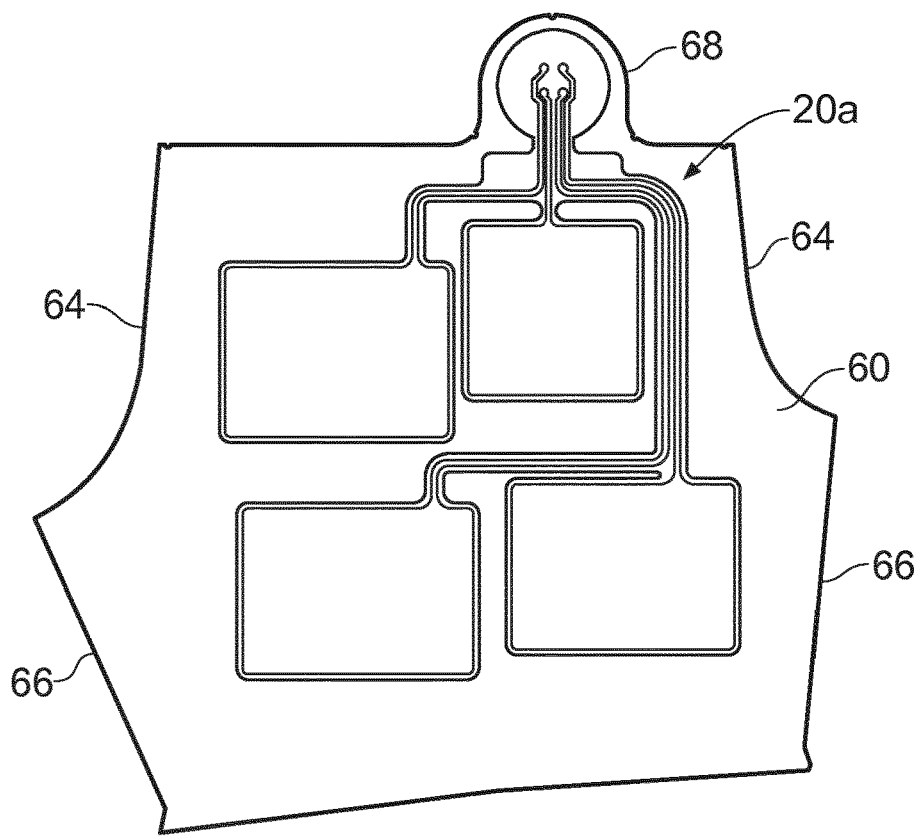
FIG. 10 is a view of an inside surface of a panel for making up a left portion of a garment according to a further embodiment of the invention.
Figure 11:
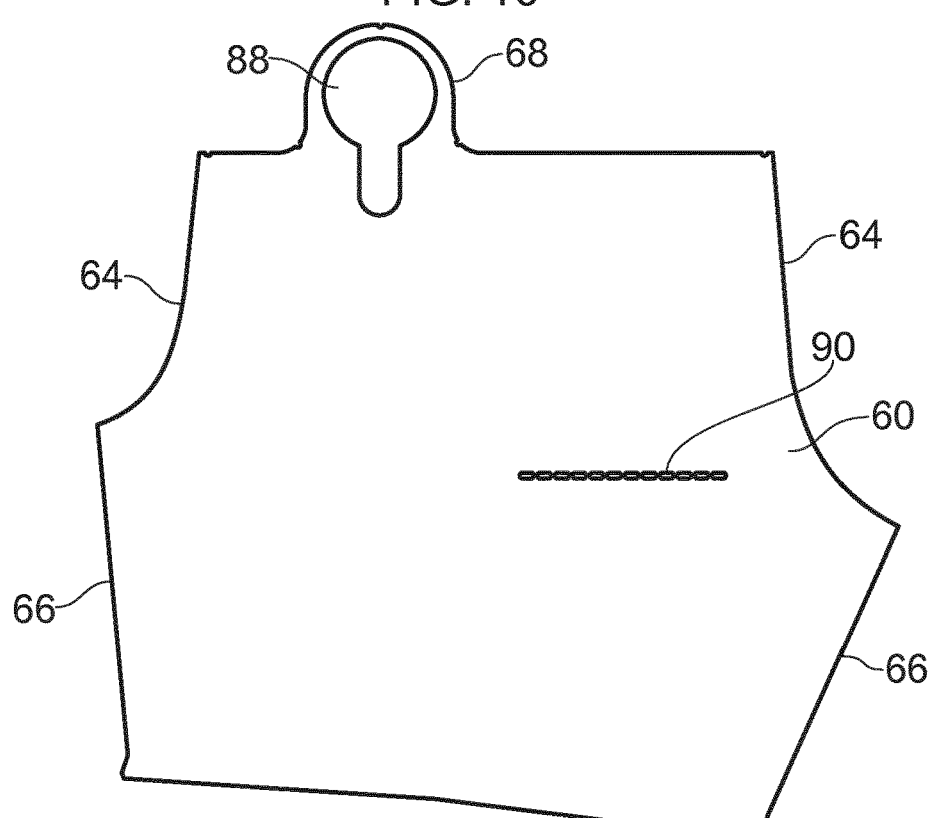
FIG. 11 is a view of an outside surface of the panel of FIG. 10.

In other arrangements, such as those illustrated in FIGS. 1 and 10-11, the tracks have a generally linear shape.

Each conductive circuit 20a, 20b is formed by printing of a series of conductive and non-conductive layers onto the fabric of the shorts (i.e. the fabric of each of the left and right leg panels 60, 62). An appropriate method of printing the conductive circuits 20a, 20b is described in GB2555592A.

The nature of the printed layers depends on the region of the conductive circuit 20a, 20b to be formed. That is, the arrangement of printed layers differs between the regions of the conductive circuit 20a, 20b in which electrical contact between the conductive circuit 20a, 20b and the skin of the user is wanted (i.e. the electrodes 22, 24, 26, 28) and the regions in which electrical contact between the conductive circuit 20a, 20b and the skin of the user is not wanted (i.e. the tracks 40).

In general terms, a series of layers is applied onto the fabric of the shorts to form electrodes. The layers applied are an adhesive layer, an encapsulation layer (non-conductive layer), a layer of conductive ink (conductive layer, which may comprise first and second conductive layers), a further encapsulation layer (non-conductive layer). The further encapsulation layer is provided over areas of the conductive ink that should not be in contact with a user's skin, and leaves areas of exposed conductive ink, as conductive areas (electrodes).

The conductive circuits 20a, 20b are generally formed by printing a series of conductive and non-conductive ink layers in a desired order onto a substrate (not shown), and then transferring the printed layers from the substrate onto the respective leg panel 60, 62 by a transfer process. For example, the substrate may be placed over the leg panel 60, 62, heat and pressure applied to transfer the printed layers to the leg panel 60, 62, and the substrate subsequently peeled away. In such embodiments the printed layers may include an adhesive layer to facilitate bonding between the printed layers and the leg panel 60, 62. In other embodiments the layers may be printed directly onto the fabric of the leg panel 60, 62.

Appropriate printing methods include, but are not limited to, screen printing, reel-to-reel printing, dot matrix printing, laser printing, cylinder press printing, ink jet printing, flexographic printing, lithographic printing, offset printing, digital printing, gravure printing or xerographic printing.

In the illustrated embodiments the tracks 40 each comprise one or more first layers of non-conductive material directly adjacent the fabric of the respective leg panel 60, 62, one or more layers of conductive material laminated over the one or more first layers of non-conductive material, and one or more second layers of non-conductive material laminated over the one or more layers of conductive material. The first and second layers of non-conductive material are wider than the layers of conductive material so that the layers of conductive material are encapsulated between the non-conductive layers. In this way, the one or more layers of conductive material can provide an electrical connection between the electrodes 22, 24, 26, 28 and the controller, via the connecting apparatus 80, while preventing any direct electrical connection between the tracks 40 and the skin of the user.

The electrodes 22, 24, 26, 28 each comprise one or more layers of non-conductive material directly adjacent the fabric of the respective leg panel 60, 62, and one or more layers of conductive material laminated over the one or more layers of non-conductive material. The one or more layers of non-conductive material are wider than the layers of conductive material so that the layers of conductive material are electrically isolated from the fabric. In this way, direct electrical connection between the electrodes 22, 24, 26, 28 and the skin of the user is possible by way of the direct contact between the user's skin and the conductive material. By forming the electrodes with printed layers in this way, stretching of the fabric in the region of each electrode is minimised, which is advantageous since this prevents undesirable increases in electrical resistance in the electrodes.

The one or more layers of conductive material of each electrode 22, 24, 26, 28 is contiguous with the one or more layers of conductive material of a respective one of the tracks 40 to thereby permit transfer of an electrical signal from the controller to each electrode 22, 24, 26, 28 via the one or more layers of conductive material.

In some embodiments the one or more layers of conductive material of each electrode 22, 24, 26, 28 comprises a first conductive layer adjacent the one or more layers of non-conductive material and a second conductive layer adjacent and overlaying the first conductive layer. The second conductive layer is thus in contact with the user's skin in use. The first conductive layer comprises a layer of a first conductive material in a mesh or grid configuration. The second conductive layer comprises a layer of a second conductive material in an unbroken, continuous configuration. The second conductive material has a lower conductivity (i.e. a higher resistivity) than the first conductive material.

Figure 12:
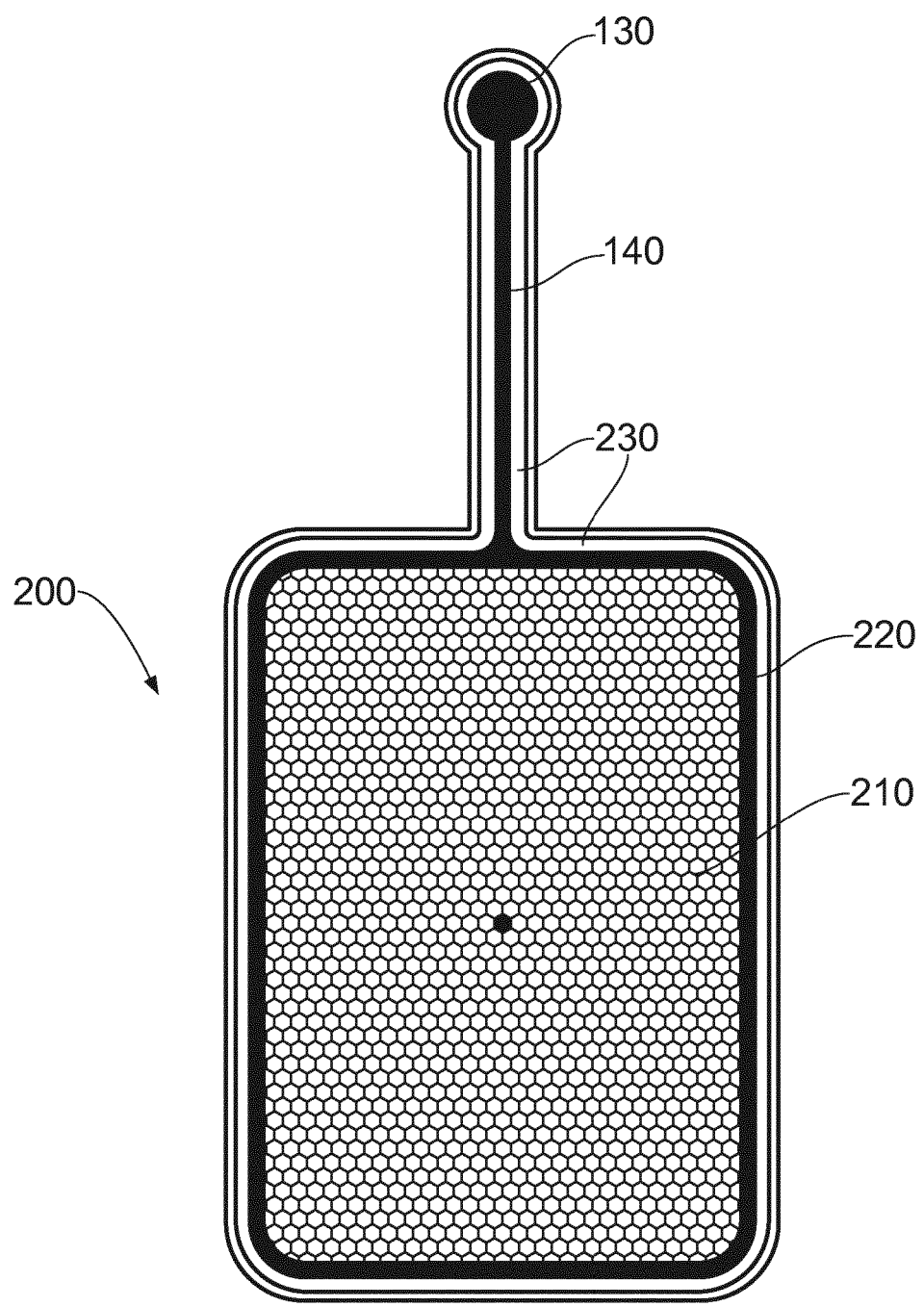
FIG. 12 is a plan view of an electrode suitable for a conductive circuit according to embodiments of the invention.

FIG. 12 illustrates such an arrangement, showing an electrode 200 suitable for use in the embodiments of FIGS. 1 to 11. That is, the electrode 200 has a configuration suitable for use in electrodes in conductive circuits according to embodiments of the invention. For example, the electrode 200 could be provided in place of electrodes 22, 24, 26, 28 described above.

The electrode 200 is electrically connected to a contact point 130 (comparable to contact point 30 described above, and having corresponding features) by conductive track 140 (comparable to conductive track 40, and having corresponding features). The assembly of electrode 200, contact point 130, and track 140 is formed from layers of conductive and non-conductive materials in the manner described above. However, in this embodiment the conductive layers of the electrode 200 are configured differently, as described further below.

The base layer of the electrode 200, contact point 130, and track 140 comprise a layer of non-conductive material 230 adjacent a fabric of the garment (not shown). The conductive layers of the electrode 200, contact point 130, and track 140 overlay the non-conductive layer 230 as described further below.

The conductive portion of the electrode 200 comprises a first layer of first conductive material 210 in the form of a mesh. That is, the first layer of first conductive material 210 comprises a regular array of uniformly-shaped and -sized regions in which no first conductive material is present. The regions of no first conductive material are hexagonal in the illustrated embodiment so that the mesh has a generally honeycomb configuration. In the illustrated embodiment the links, or tracks, that interconnect at nodes to form the mesh configuration are each approximately 0.5 mm wide and 4 mm long. It is envisaged that suitable ranges are widths from 0.1 to 1.0 mm and lengths from 2 to 8 mm.

A second layer of second conductive material 220 overlays the first layer 210. The second layer 220 overlaps with the first layer 210 only in a band, or strip, around the periphery of the first layer 210, so that a central region of the first layer 210 is uncovered by the second layer 220. In this way, both the second layer of second conductive material 220 and the central region of the first layer of first conductive material 210 are in contact with a user's skin during use. In other embodiments the second layer 220 may completely, or substantially, overlap the first layer 210 so that only the second layer 220 is in contact with the user's skin during use.

The second layer of second conductive material 220 is contiguous with the layers of conductive material forming the conductive track 140 and contact point 130. Thus, these regions of conductive material can be formed as a unitary feature from one or more layers of second conductive material.

As described above, the second conductive material has a lower conductivity (i.e. a higher resistivity) than the first conductive material, and is accordingly generally less expensive to purchase. Thus, the use of the more expensive first conductive material can be restricted to the first layer of conductive material 210. By way of example, the second conductive material may comprise carbon and/or copper, while the first conductive material may comprise silver.

The one or more layers of non-conductive material preferably comprise one or more non-conductive ink layers. A suitable printing ink comprises a water based printing ink, an ultraviolet-cured printing ink, a solvent based ink, or a latex printing ink, for example. A particularly preferred ink for the non-conductive layers comprises a screen-printable ink of CMYK toner.

The one or more layers of conductive material preferably comprise one or more conductive ink layers. The conductive material may comprise an electrically conductive metal, such as silver, silver chloride, copper or combinations or alloys thereof. Suitable conductive inks may be supplied by Engineering Materials Systems, Inc. under the brand name Engineered Conductive Materials (ECM)™.

Each of the layers of conductive or non-conductive material may have a thickness of 0.5 mm or less, 0.4 mm or less, 0.3 mm or less, 0.2 mm or less, 0.1 mm or less.

Each conductive circuit 20a, 20b is provided with a connecting apparatus 80 to connect it to a controller (not shown). The controller may be as described in WO2007138071. The connecting apparatus 80 may, for example, be a wire with appropriate connectors. In the illustrated embodiments the connecting apparatus 80 comprises left and right connectors 82 that provide an electrical connection between the conductive circuits 20a, 20b and left and right cables 86.

Each connector 82 comprises a rigid two-part assembly. A first part of each connector 82 is durably fixed to a respective leg panel 60, 62 so that each of four electrical connecting pins within the first part form an electrical connection with a respective one of the four electrical contact points 30 of the respective conductive circuit 20a, 20b. A second part of each connector 82 can be removably connected to the first part to create an electrical connection therebetween. For example, one or both of the first and second parts may comprise magnets to facilitate an easy interconnection. In such embodiments each connector 82 may comprise magnets with opposing polarities to ensure that a user connects the correct first and second parts together, and to prevent incorrect connection. The second part of each connector 82 provides a durable connection to the respective cable 86, which comprises a jack for connection of the shorts 100 with the controller (not shown).

While it is desirable for the fabric of the shorts 100 to be stretchy to enable easy use by users and to ensure a good contact between the user's skin and the electrodes, it has been found that it is desirable to restrict stretch of the fabric in the region of the connectors 82 in order to ensure a reliable electrical connection between the controller and the conductive circuits 20a, 20b. In the illustrated embodiments this has been achieved by means of left and right rubber sheet layers 88 which are each sandwiched between the respective connector 82 and the fabric of the respective leg panel 60, 62. In preferred arrangements the rubber sheet layers 88 (and the fabric of the respective leg panel 60, 62) are each sandwiched between rigid portions of the first part of the respective connector 82. This arrangement not only provides a reliable electrical connection, but also serves to prevent water ingress into the connector 82, for example during washing of the shorts 100.

Electrical connectivity between the electrodes 22, 24, 26, 28 and the user's skin is preferably maximised by use of an electrolytic fluid. For example, the user may spray the electrodes with electrolytic solution or saline solution prior to use.

The garment described herein has been tested by a user and its effectiveness compared with the prior art device described above. The user checked the power level needed to reach the maximum stimulation that the user could tolerate. The user found that, when using the current device and the prior art device with the same controller, a maximum stimulation level was achieved with the current device at a much lower power level than needed for the prior art device. This may be because in applying the various layers to the garment's fabric, the modulus of the fabric in those areas in increased. This means that whilst the garment is easy to put on, the conductive areas remain tightly pressed against the body.

The invention claimed is:

1. A wearable garment for a human or animal body, the garment comprising a stretch fabric and one or more conductive circuits, each conductive circuit comprising:
   one or more electrodes for delivering an electromagnetic signal to a human or animal body wearing the garment;
   one or more connection tracks, each connection track providing an electrically conductive path between a respective one of the one or more electrodes and an electrical contact configured to enable connection to a controller arranged to supply an electromagnetic signal to the one or more electrodes; and
   a base,
   the one or more electrodes and the one or more connection tracks each comprising:
   one or more printed non-conductive layers comprising a non-conductive ink deposited directly on the base;
   at least one printed conductive layer comprising a conductive ink deposited on the one or more printed non-conductive layers; and
   one or more printed encapsulating non-conductive layers comprising a non-conductive ink deposited on the at least one printed conductive layer,
   wherein the stretch fabric of the garment forms the base of the one or more conductive circuits, and
   wherein the one or more printed encapsulating non-conductive layers are deposited on the at least one printed conductive layer throughout the one or more connection tracks to thereby encapsulate the one or more connection tracks, but are not deposited on the at least one printed conductive layer at each of the one or more electrodes such that the at least one printed conductive layer is configured to contact skin of a human or animal body at the one or more electrodes in use.

2. The garment according to claim 1, wherein the garment is configured to be wearable on a lower body region of a human or animal body, the garment comprising two conductive circuits including a first conductive circuit having one or more electrodes configured to contact a left side of the body and a second conductive circuit having a corresponding one or more electrodes configured to contact a right side of the body.

3. The garment according to claim 1, wherein there are no seams that dissect any of the one or more conductive circuits.

4. The garment according to claim 1, comprising a left panel carrying a first conductive circuit of the one or more conductive circuits and a right panel carrying a second conductive circuit of the one or more conductive circuits, the left and right panels encircling left and right thighs of the body in use.

5. The garment according to claim 1, further comprising one or more visual indicators configured to be aligned with a known body feature in use.

6. The garment according to claim 1, further comprising one or more of a power supply, control unit and controller for providing an electromagnetic signal to the one or more electrodes of the one or more conductive circuits.

7. The garment according to claim 1, wherein the printed conductive layer comprises a plurality of regions in which conductive material is not present.

8. The garment according to claim 1, wherein each conductive circuit comprises two printed conductive layers: a first printed conductive layer; and a second printed conductive layer adjacent the first conductive material, the second conductive layer being configured to contact the skin of the human or animal body at the one or more electrodes in use.

9. The garment according to claim 8, wherein the second printed conductive layer comprises or consists of a second conductive material and the first printed conductive layer comprises or consists of a first conductive material different to the second conductive material.

10. The garment according to claim 9, wherein the first and second conductive materials have different conductivities, the first conductive material having a higher conductivity than the second conductive material.

11. A method of stimulating muscle activity comprising the step of applying the wearable garment according to claim 1 to the human or animal body.

12. A method of detecting one or more of muscle stimulation, contraction, and relaxation, the method comprising applying the wearable garment according to claim 1 to the human or animal body.

13. A method of treating incontinence, the method comprising applying the wearable garment according to claim 1 to the human or animal body.

* * * * *